US010004535B2

(12) United States Patent
Khubani

(10) Patent No.: US 10,004,535 B2
(45) Date of Patent: Jun. 26, 2018

(54) ABRASIVE SKIN TREATMENT DEVICE

(71) Applicant: Telebrands Corp., Fairfield, NJ (US)

(72) Inventor: Ajit Khubani, Saddle River, NJ (US)

(73) Assignee: Telebrands Corp., Fairfield, NJ (US)

( * ) Notice: Subject to any disclaimer, the term of this patent is extended or adjusted under 35 U.S.C. 154(b) by 7 days.

(21) Appl. No.: 15/045,974

(22) Filed: Feb. 17, 2016

(65) Prior Publication Data

US 2017/0209174 A1 Jul. 27, 2017

Related U.S. Application Data

(63) Continuation-in-part of application No. 29/552,947, filed on Jan. 27, 2016, now Pat. No. Des. 765,914.

(51) Int. Cl.
A45D 29/18 (2006.01)
A61B 17/54 (2006.01)
A61B 90/00 (2016.01)
A61B 17/32 (2006.01)
A61B 17/00 (2006.01)

(52) U.S. Cl.
CPC .............. A61B 17/54 (2013.01); A61B 17/32 (2013.01); A61B 90/36 (2016.02); A45D 2200/1054 (2013.01); A61B 2017/0069 (2013.01); A61B 2017/00398 (2013.01); A61B 2017/00424 (2013.01); A61B 2017/00747 (2013.01); A61B 2017/00761 (2013.01); A61B 2017/320004 (2013.01)

(58) Field of Classification Search
CPC .................... A61B 17/54; A61B 90/36; A41B 2017/00424; A41B 2017/320004; A41B 2017/00761; A45D 29/05; A45D 29/14; B24B 23/02; Y10T 403/32196; Y10T 403/32311; Y10T 403/32565–403/32581; Y10T 403/32631
See application file for complete search history.

(56) References Cited

U.S. PATENT DOCUMENTS

| 2,676,389 | A | 4/1954 | Testi |
| 2,867,214 | A | 1/1959 | Wilson |
| D447,282 | S | 8/2001 | Yiu |
| D447,881 | S | 9/2001 | Yiu |
| 6,301,786 | B1 | 10/2001 | Oswald |
| D450,157 | S | 11/2001 | Yiu |
| 6,471,712 | B2 | 10/2002 | Burres |
| 6,892,457 | B2 | 5/2005 | Shiba |

(Continued)

FOREIGN PATENT DOCUMENTS

| CA | 2828671 | 9/2012 |
| CA | 2848080 | 9/2012 |

(Continued)

OTHER PUBLICATIONS

Panasonic Arc 3 Blade Shaver, available at www.shop.panasonic.com, accessed Sep. 25, 2014.

(Continued)

Primary Examiner — Rachel Steitz
(74) Attorney, Agent, or Firm — Cooper & Dunham, LLP

(57) ABSTRACT

An abrasive skin treatment device including a handle portion, a head portion including an exfoliating element, and a unitary pivoting mechanism providing relative movement between the handle portion and the head portion along at least two planes.

10 Claims, 4 Drawing Sheets

(56) References Cited

U.S. PATENT DOCUMENTS

| | | | |
|---|---|---|---|
| 7,020,966 B2 | 4/2006 | Shiba | |
| 7,060,119 B1 | 6/2006 | Haider | |
| 7,334,338 B2 | 2/2008 | Shiba | |
| 7,461,456 B2 | 12/2008 | Tsushio | |
| 7,644,589 B2 | 1/2010 | Habatjou | |
| 7,739,798 B2 | 6/2010 | Iwasaki | |
| 7,832,104 B2 | 11/2010 | Yamasaki | |
| D640,416 S | 6/2011 | Watson | |
| D640,830 S | 6/2011 | Watson | |
| D640,831 S | 6/2011 | Watson | |
| D641,104 S | 7/2011 | Watson | |
| 8,011,102 B2 | 9/2011 | Sato | |
| 8,028,418 B2 | 10/2011 | Sagawa | |
| D655,042 S | 2/2012 | Watson | |
| D655,861 S | 3/2012 | Watson | |
| 8,181,349 B2 | 5/2012 | Sagawa | |
| 8,205,343 B2 | 6/2012 | Winter | |
| D663,480 S | 7/2012 | Watson | |
| D673,730 S | 1/2013 | Watson | |
| 8,479,397 B2 | 7/2013 | Sato | |
| 8,551,117 B2 | 10/2013 | Yiu | |
| 8,627,574 B2 | 1/2014 | Shimizu | |
| 8,661,688 B2 | 3/2014 | Shigeta | |
| D706,487 S | 6/2014 | Yiu | |
| D706,986 S | 6/2014 | Yiu | |
| 8,745,883 B2 | 6/2014 | Murgida | |
| 8,938,885 B2 | 1/2015 | Stevens | |
| 8,978,258 B2 | 3/2015 | Patel | |
| D726,372 S | 4/2015 | Yiu | |
| 9,060,583 B2 | 6/2015 | Barraclough | |
| 2002/0107527 A1* | 8/2002 | Burres | A45D 29/14 606/131 |
| 2004/0254587 A1 | 12/2004 | Park | |
| 2007/0125097 A1 | 6/2007 | Habatjou | |
| 2007/0227007 A1 | 10/2007 | Fukutani | |
| 2008/0034591 A1 | 2/2008 | Fung | |
| 2010/0018057 A1 | 1/2010 | Fukutani | |
| 2012/0226289 A1 | 9/2012 | Yiu | |
| 2014/0025091 A1 | 1/2014 | Yiu | |
| 2015/0374409 A1 | 12/2015 | Chopdat | |
| 2016/0058659 A1* | 3/2016 | Angelov | A61H 23/0263 601/73 |

FOREIGN PATENT DOCUMENTS

| | | |
|---|---|---|
| CN | 102958461 | 3/2012 |
| DE | 29710333 U1 | 9/1997 |
| DE | 202012012850 U1 | 2/2014 |
| WO | WO2012120373 | 9/2012 |

OTHER PUBLICATIONS

Panasonic Arc 4 Blade Shaver, available at www.shop.panasonic.com, accessed Sep. 25, 2014.
Panasonic ES7056S Vortex Shaver, available at www.newegg.com, accessed Sep. 26, 2014.
Nair Spa Clay Roll-On Wax, available at www.drugstore.com, accessed Aug. 24, 2014.
Povos PS6108, available at www.newegg.com, accessed Sep. 26, 2014.
Povos PS6128, available at www.newegg.com, accessed Sep. 26, 2014.
Emjoi Micro-Pedi, available at www.amazon.com, accessed Sep. 24, 2014.
Emjoi Micro-Pedi Power, available at www.amazon.com, accessed Sep. 24, 2014.
Ckeyin Powerful Rechargeable Foot Spa, available at www.amazon.com, accessed Sep. 24, 2014.
Epilady Legend 4 Epilator, available at www.drugstore.com, accessed Sep. 24, 2014.
Panasonic ES2207P, available at www.amazon.com, accessed Sep. 24, 2014.
Emjoi Divine Epilator, available at www.amazon.com, accessed Sep. 24, 2014.
20124 New Electric Foot Perfect Pedicare, available at www.alibaba.com, accessed Sep. 25, 2015.
Braun Series 5 5030S Electric Shaver, available at www.walgreens.com, accessed Sep. 26, 2014.
Panasonic ARC3 Wet Dry Pivoting Head Shaver, www.bestbuy.com, accessed Sep. 26, 2014.
Supplementary European Search Report EP20120754594, publication No. EP2680768 A4, published Feb. 12, 2014.
Personal Pedi, available at www.personalpedi.com, accessed on Oct. 10, 2014.
Conair Women's Dual Foil Battery Shaver, available at www.drugstore.com, accessed Sep. 24, 2014.
2014 New Electrical Foot File, available at www.aliexpress.com, accessed Sep. 24, 2014.
Micro Pedi Cordless, available at www.target.com, accessed Sep. 24, 2014.
Bestpriceam Women Wet Dry Foot Care Electric Callus Remover, available at www.amazon.com, accessed Sep. 24, 2014.
Electrical Callus Remover with Beautiful Appearance, available at www.alibaba.com, accessed Sep. 25, 2014.
New Professional Electric Callus Removeer 7670, available at www.alibaba.com, accessed Sep. 25, 2014.
Jinding Electric Callus Remover, available at www.alibaba.com, accessed Sep. 25, 2014.
Electric Callus Remover Detachable Roller Heads, available at www.ningbogreat.manufacturer.globalsources.com, accessed Sep. 25, 2014.
Electronic Rough Callus Hard Foot Skin Remover Kit, available at www.dhgate.com, accessed Sep. 25, 2014.
Written Opinion of International Search Authority PCT/US17/16942, published Mar. 13, 2017.
International Search Report PCT/US17/16942, published Mar. 13, 2017.

* cited by examiner

ABRASIVE SKIN TREATMENT DEVICE

CROSS-REFERENCE TO PRIOR APPLICATIONS

This applications is a continuation-in-part application of U.S. Design patent application Ser. No. 29/552,947, filed on Jan. 27, 2016, which is hereby incorporated by reference herein in its entirety.

TECHNICAL FIELD

Embodiments of the present invention generally relate to a skin treatment device. More specifically, embodiments of the present invention relate to an abrasive skin treatment device for removing calluses and dead skin.

BACKGROUND

A callus is a thickened and/or hardened part of the skin, and can often be found on hands and feet. Often, the callus is dead skin. Calluses can appear on feet due to rubbing from poorly fitting shoes or excessive exercise, and can commonly be found on the heel, sides of the toes, or the ball of the foot. Calluses can appear on hands from rubbing and pinching of skin that occurs while lifting heavy objects or from regular weight-lifting, and can commonly be found on the palms right below the fingers.

There are a variety of known methods of removing calluses, most of these methods involve scraping, shaving, or rubbing the calluses until the dead skin has been removed. Other methods include softening the callus by soaking the callus in warm water or using lotions or creams. Known devices used to remove calluses or dead skin, include pumice stones, foot files, and a variety of abrasive devices. Some of these devices are electrically powered, and include a rotating or vibrating abrasive head.

The known abrasive devices have several drawbacks. Due to the shape of the abrasive or exfoliating surface, known devices are often unable to adjust to the contours or curvature of the surfaces where calluses generally occur. Accordingly, either the user often has to adjust their grip or move their wrist in order to optimize the angle at which the abrasive or exfoliating surface is contacting the callus or dead skin, or the user has to repeatedly cover the contoured areas several times with the abrasive device to effectively remove the callus or dead skin.

SUMMARY

Embodiments of the present invention can provide an abrasive skin treatment device. The abrasive skin treatment device can include a handle portion, a head portion including an exfoliating element, and a unitary pivoting mechanism enabling relative movement between the handle portion and the head portion along at least two planes.

The unitary pivoting mechanism can be substantially spherical. The head portion can pivot about the unitary pivoting mechanism and relative to the handle portion upon application of a force to at least one of the head portion and the handle portion. The head portion can also be configured to pivot at the unitary pivoting mechanism and relative to the handle portion in 360 degrees. Further, the head portion can include a light. The light can be a light emitting diode. The head portion can also include a motor and power supply.

Additionally, the exfoliating element can be removably coupled to the head portion. The exfoliating element can be also be substantially cylindrical. The exfoliating element can also be rotatable coupled to the head portion.

Another embodiment of the present invention can provide a unitary pivoting mechanism having a first end and a second end, a handle portion coupled to the first end of the unitary pivoting mechanism such that the handle portion can pivot relative to the unitary pivoting mechanism along a first plane, and a head portion including an exfoliating element, the head portion coupled to the second end of the unitary pivoting mechanism such that the head portion can pivot relative to the unitary pivoting mechanism along a second plane, the first plane and the second plane being different.

The unitary pivoting mechanism can be substantially spherical. The head portion can pivot about the unitary pivoting mechanism and relative to the handle portion upon application of a force to at least one of the head portion and the handle portion. The head portion can also be configured to pivot at the unitary pivoting mechanism and relative to the handle portion in 360 degrees. Further, the head portion can include a light. The light can be a light emitting diode. The head portion can also include a motor and power supply.

Additionally, the exfoliating element can be removably coupled to the head portion. The exfoliating element can be also be substantially cylindrical. The exfoliating element can also be rotatable coupled to the head portion.

BRIEF DESCRIPTION OF THE DRAWINGS

The features and advantages of the present invention can be more readily understood from the following detailed description with reference to the accompanying drawings, wherein:

FIG. 4B is an illustration of an exemplary head portion in accordance with embodiments of the present invention.

DETAILED DESCRIPTION OF THE EMBODIMENTS

Embodiments of the present invention generally relate to a skin treatment device. More specifically, embodiments of the present invention relate to a pivoting abrasive skin treatment device for removing calluses and dead skin.

Figure 1:
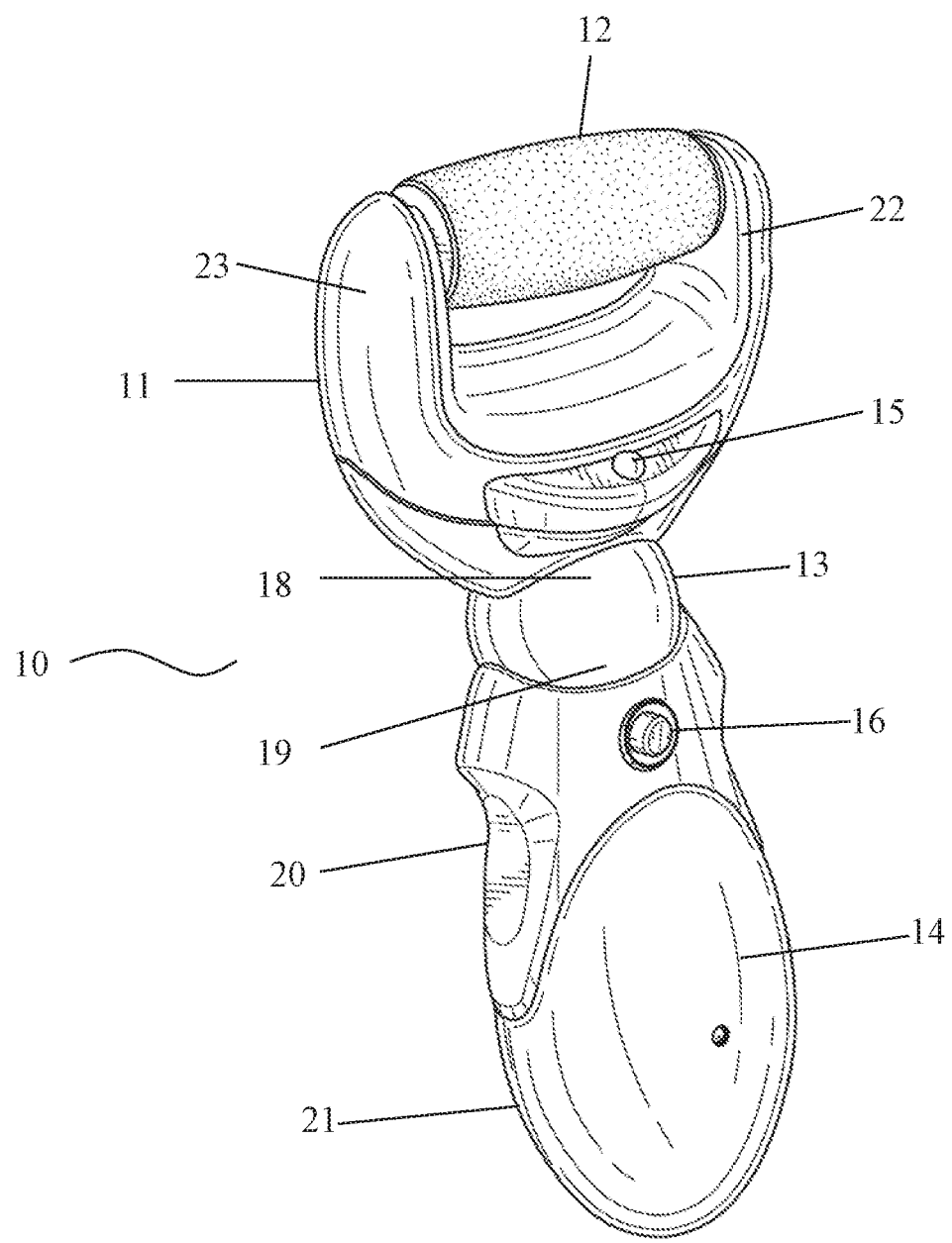
FIG. 1 is an isometric view illustrating an embodiment of the present invention.

FIG. 1 shows an exemplary skin treatment device 10 according to exemplary embodiments of the present invention. As shown in FIG. 1, skin treatment device 10 can include a handle portion 14, a head portion 11, an exfoliating element 12, and a unitary pivoting mechanism 13. Exfoliating element 12 can include an abrasive surface that is suited for removing a callus/hardened skin and the unitary pivoting mechanism 13 can enable the head portion 11 to pivot relative to the handle portion 14. Additionally, as shown in FIG. 1, skin treatment device 10 can optionally include switch 16 and a light 15. In operation, a user can hold skin treatment device 10 via handle portion 14 and position exfoliating element 12 against a callus/hardened skin or other target area the user desires to treat. In use, the user may turn skin treatment device 10 ON via switch 16, thereby activating a motor which drives exfoliating element 12. For example, the motor may cause exfoliating element 12 to move in a reciprocating pattern (e.g., linear, rotational) or in a rotational pattern at a rate sufficient to remove the callus/hardened skin or otherwise treat the target area when the moving exfoliating element 12 is in contact with the target area. As the user treats the callus/hardened skin or other target area, pivoting mechanism 13 may enable relative movement between handle portion 14 and head portion 11 to conform and adjust to contours/irregularities of the surface of the target area and the movement of skin treatment device 10 introduced by the user.

Figure 2:
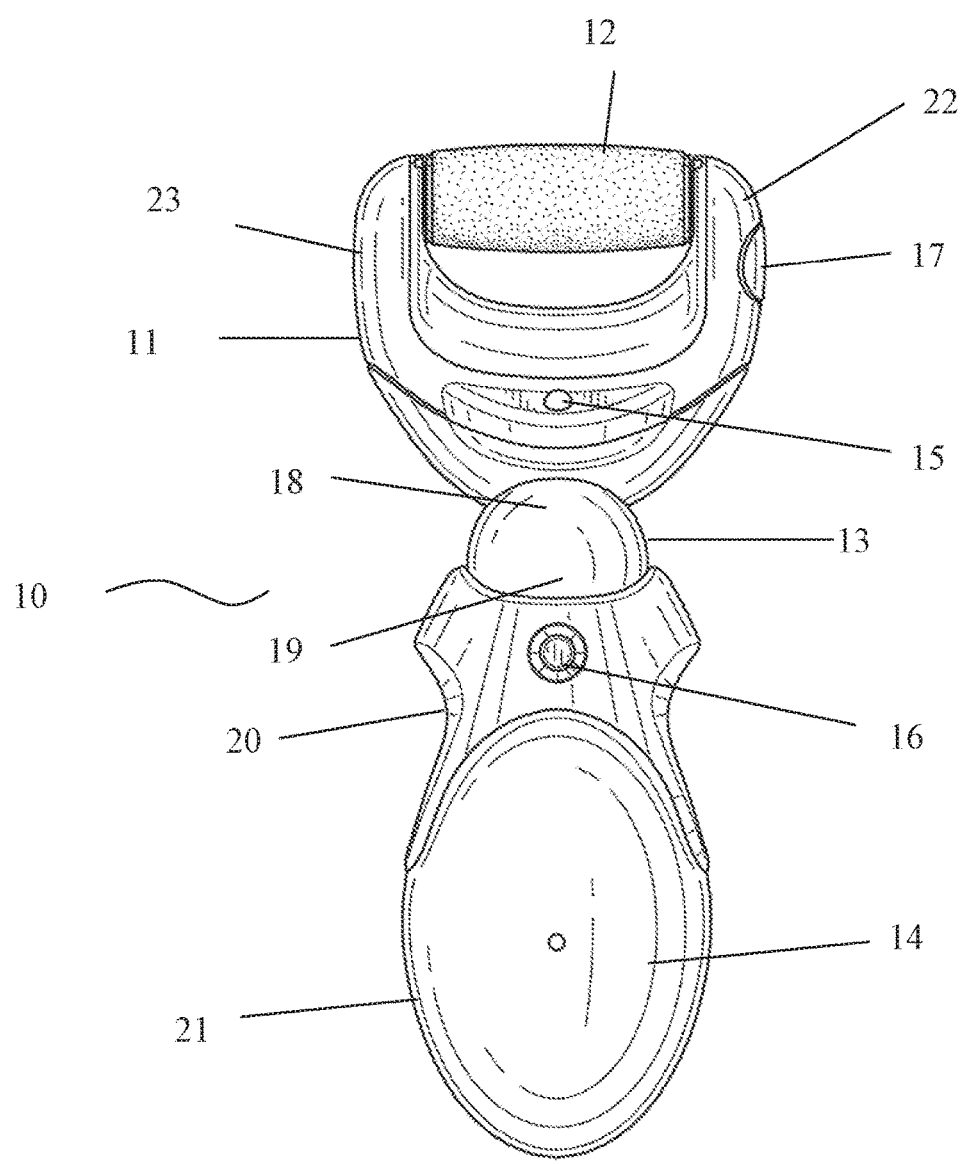
FIG. 2 is a side view illustrating an embodiment of the present invention.

As shown in FIGS. 1 and 2, skin treatment device 10 includes exfoliating element 12. Exfoliating element 12 includes an abrasive surface and is articulated by skin treatment device 10 so that the motion of exfoliating element 12 against a callus/hardened skin, or other target area, can remove/exfoliate the skin from the target area. Exfoliating element 12 may be articulated by a motor of skin treatment device 10, and may be articulated in any manner. For example, exfoliating element 12 may rotate, move back and forth linearly, move back and forth along an arc, or move in some other reciprocating motion. Further, exfoliating element 12 may to releasably coupled so that exfoliating element 12 can be replaced as the abrasive surface becomes worn through use. As shown in FIGS. 1-3, exfoliating element 12 may be substantially cylindrical. Additionally, exfoliating element 12 can include different materials and different levels of abrasiveness/coarseness for different applications.

As shown in FIGS. 1 and 2, head portion 11 secures and positions exfoliating element 12. Head portion 11 can be configured to secure and position exfoliating element 12 in any position or configuration that may be convenient and/or ergonomic for the operation of skin treatment device 10. For example, as shown in FIGS. 1 and 2, head portion 11 may include two arms 22 and 23, which can include coupling elements for receiving and coupling exfoliating element 12 there-between. Alternatively, head portion 11 can include any configuration to secure and position exfoliating element 12 for any desired orientation and mode of operation. According to certain embodiments of the present invention, exfoliating element 12 can be coupled to head portion 11 via coupling elements. Exfoliating element 12 may be fixedly coupled to the head portion 11. Alternatively, the exfoliating element 12 can be rotatably coupled to the head portion 11. Exfoliating element 12 may be coupled to head portion 11 via any suitable coupling element, such as, e.g., a saddle joint, a ball-and-socket joint, a tension spring, or the like.

Figure 3A:
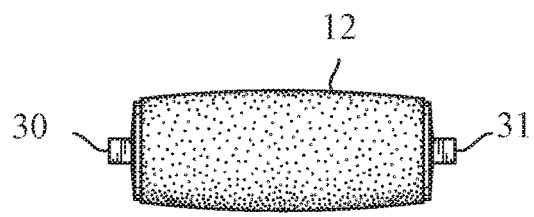
FIG. 3A is an illustration of an exemplary exfoliating element in accordance with embodiments of the present invention.
Figure 3B:
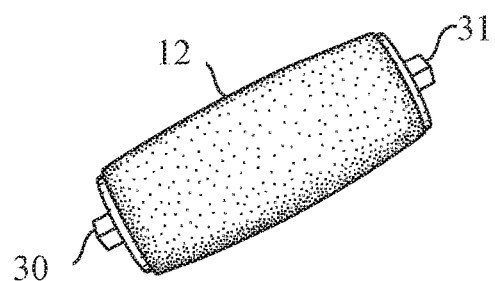
FIG. 3B is an illustration of an exemplary exfoliating element in accordance with embodiments of the present invention.
Figure 4A:
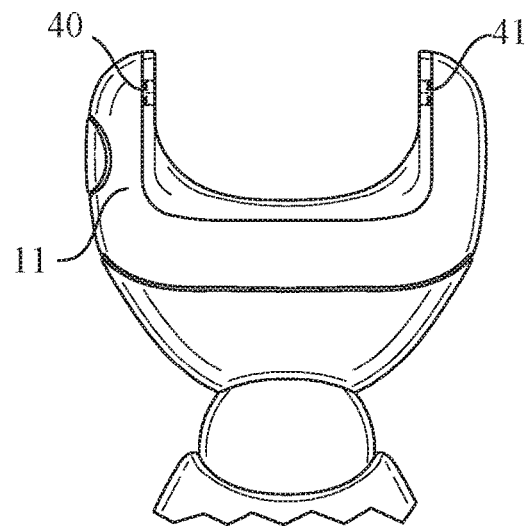
FIG. 4A is an illustration of an exemplary head portion in accordance with embodiments of the present invention.
Figure 4A:
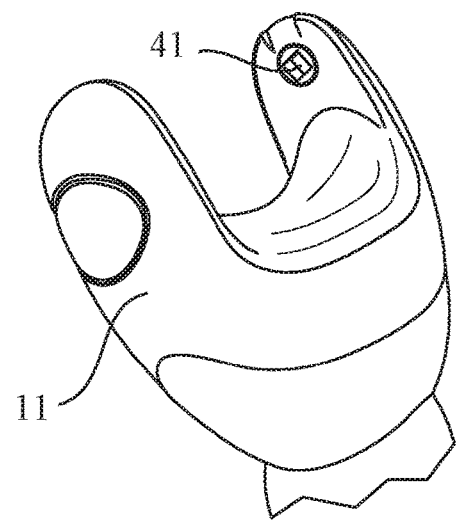

FIGS. 3A and 3B show exfoliating element 12 and FIGS. 4A and 4B show exemplary head portion 11 coupling elements 40 and 41 according to embodiments of the present invention. As shown in FIGS. 3A and 3B, exfoliating element 12 may be substantially cylindrical and may include coupling elements 30 and 31 for coupling exfoliating element 12 to head portion 11 via coupling elements 40 and 41.

For example, coupling elements 30 and 31 may engage coupling elements 40 and 41, thereby enabling exfoliating element 12 to be releasably coupled to head portion 11. Alternatively, coupling elements 30 and 31 may engage coupling elements 40 and 41 to be permanently coupled to head portion 11. According to one embodiment, coupling elements 30 and 31 may include features configured to engage complimentary features of coupling elements 40 and 41 on head portion 11. For example, coupling elements 30 and 31 may include spring loaded projections configured to compress and engage recesses of coupling elements 40 and 41 formed in head portion 11. Alternatively, coupling elements 30 and 31 may include recesses configured to receive projections of coupling elements 40 and 41 included on head portion 11. Although FIGS. 3A, 3B, 4A, and 4B show exfoliating element 12 to be substantially cylindrical, coupling elements 30 and 31 to include projections, and coupling elements 40 and 41 to include recesses, exfoliating element 12 and coupling elements 30, 31, 40, and 41 can take any shape, form, or mechanism that facilitates the desired functionality.

As noted above, exfoliating element 12 can be removably coupled to head portion 11 to enable replacement of exfoliating element 12 and to provide adaptability for different applications. Accordingly, as illustrated in FIG. 2, the head portion 11 can optionally house including a release mechanism 17 by which to disengage the coupling exfoliating element 12 to head portion 11, thereby releasing exfoliating element 12 from head portion 11. For example, release mechanism 17 may include a release button, which when activated, is configured to disengage coupling elements 30 and 31 from coupling elements 40 and 41, thereby disengaging exfoliating element 12 from the head portion 11. The release mechanism may be any of the mechanisms known in the art that can be used to disengage exfoliating element 12 from the head portion 11, such as, e.g., a spring-loaded button, snap button, or the like. Additionally, according to embodiments of the present invention, the head portion 11 can optionally house a light 15 to illuminate the callus/hardened skin or target area. The light may be beneficial to a user because it can allow them to better view the target area. In a preferred embodiment the light 15 can include a light emitting diode. Additionally, the light 15 can be turned on/off using a switch 16. According to embodiments of the present invention, the switch 16 can be disposed on the handle portion 14. Alternatively, the switch 16 can be disposed on head portion 16 or unitary pivoting mechanism 13.

According to embodiments of the present invention, the handle portion 14 can be shaped in any shape or size to comfortably fit in a user's hand. For example, the handle portion 14 may be cylindrical, cuboidal, ball-shaped, spherical, or the like. Additionally, the handle portion 14 can be shaped in a variety of different sizes for different sized users. Alternatively, in a preferred embodiment, as shown in FIGS. 1 and 2, the handle portion 14 may be contoured and designed to ergonomically fit in a user's hand to minimize discomfort and fatigue, and to maximize control over the device. For example, as illustrated in FIGS. 1 and 2, the handle portion 14 can have indentations 20 to accommodate the thumbs of a user, and a wider, oval base 21 to allow the device 10 to securely sit in the palm of a user.

Additionally, the handle portion 14 and/or the head portion 11 can house a motor assembly to electrically power the rotational or reciprocating motion of the exfoliating element 12. The motor assembly may include various components such as, e.g., gears, linkages, etc. that enable the motor to drive exfoliating element 12. The motor assembly may be powered by any electrical power, for example, by battery power, by AC power via a plug adapter, etc. The supplied electrical power may be housed anywhere within skin treatment device 10. According to embodiments of the present invention and as illustrated in the Figures, the handle portion 14 can house a switch 16 to turn the motor assembly on/off. Alternatively, switch 16 can be disposed on head portion 11 or unitary pivoting mechanism 13.

According to embodiments of the present invention, skin treatment device 10 preferably includes unitary pivoting mechanism 13, which allows relative movement between handle portion 14 and head portion 11. According to certain exemplary embodiments, unitary pivoting mechanism 13 can provide head portion 11 to be independently adjusted relative to the handle portion 14 and head portion 11 can be adjustably fixed in that position. The unitary pivoting mechanism 13 can provide the head portion 11 to pivot relative to the handle portion 14 when a force is applied to either the handle portion 14 and/or the head portion 11. The unitary pivoting mechanism 13 can enable the head portion 11 to pivot in one or more planes. For example, the unitary pivoting mechanism 13 can enable the head portion 11 to pivot relative to the handle portion 14 in one plane. Alternatively, the unitary pivoting mechanism 13 can enable the head portion 11 to pivot relative to the handle portion 14 in two planes. Similarly, the unitary pivoting mechanism 13 can enable the head portion 11 to pivot relative to the handle portion 14 in three, four, or five planes. Alternatively, the unitary pivoting mechanism 13 can enable the head portion 11 to pivot relative to the handle portion 14 in 360 degrees.

Unitary pivoting mechanism 13 can be any mechanism by which the relative motion between the handle portion 14 and head portion 11 can be provided. For example, the unitary pivoting mechanism 13 can be ball-shaped or substantially spherical. According to embodiments of the present invention, the unitary pivoting mechanism 13 can be substantially enclosed within the handle portion 14 and/or head portion 11 so that at least a portion of unitary pivoting mechanism 13 is substantially hidden from user's view. Alternatively, unitary pivoting mechanism 13 can include any mechanism that may enables head portion 11 to pivot relative to handle portion 14, including, e.g., a saddle joint, a ball-and-socket joint, a tension spring, or the like. The multiple planes of movement can also be provided via any mechanism. For example, unitary pivoting mechanism 13 can include a first end 18 and a second end 19. The first end may be coupled to head portion 11 and may provide relative motion between unitary pivoting mechanism 13 and head portion 11 along a first plane while being fixed relative along other planes. Similarly, the second end may be coupled to handle portion 14 and may provide relative motion between unitary pivoting mechanism 13 and handle portion 14 along a second plane while being fixed relative along other planes. Further, the first plane and the second plane may be different, thus enabling relative movement in at least the first and second planes. This pivoting mechanism can be beneficial where the callus/hardened skin or the target area to be treated is contoured or has an irregular surface. The pivoting mechanism can also be beneficial where it can enable consistent contact with the callus/hardened in view of the user moving skin treatment device 10.

Figure 5:
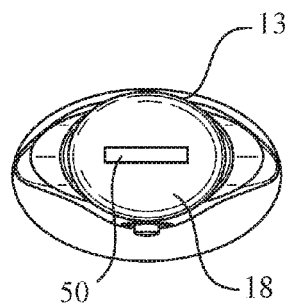
FIG. 5 is a frontal illustration of an exemplary unitary pivoting mechanism in accordance with embodiments of the present invention.
Figure 6:
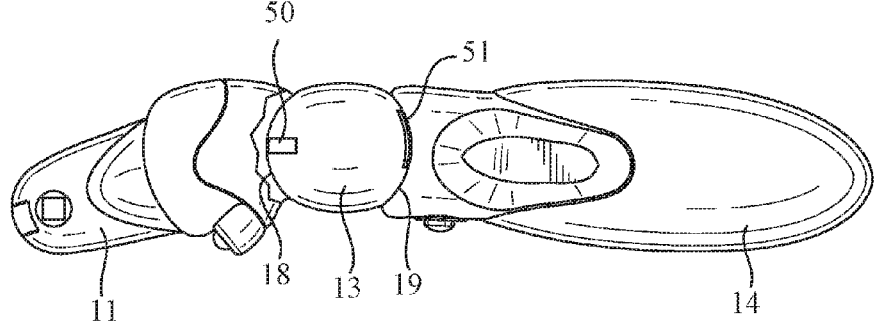
FIG. 6 is an illustration of an exemplary unitary pivoting mechanism in accordance with embodiments of the present invention.
Figure 7:
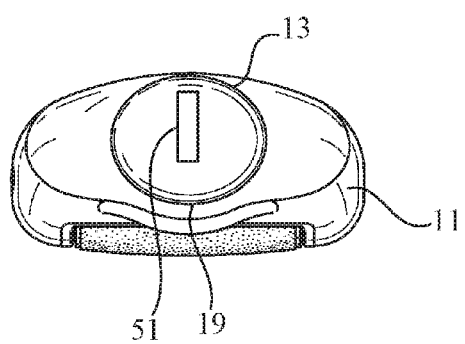
FIG. 7 is an illustration of an exemplary unitary pivoting mechanism in accordance with embodiments of the present invention.

FIGS. 5-7 show unitary pivoting mechanism 13 according to an embodiment of the present invention. As shown in FIGS. 5-7, unitary pivoting mechanism 13 may include first end 18 having a coupling mechanism 50 and second end 19 having coupling mechanism 51. Coupling mechanisms 50 and 51 may enable head portion 11 and handle portion 14 to be coupled to unitary pivoting mechanism 13 and may also define a range of motion or pivoting between unitary pivoting mechanism 13 and head portion 11 and handle portion 14. For example, coupling mechanisms 50 and 51 may include elongated openings or recesses which engage with complimentary features of head portion 11 and handle portion 14, respectively, and facilitate pivoting between unitary pivoting mechanism 13 and head portion 11 and handle portion 14. For example, as shown in FIGS. 5 and 6, coupling mechanism 50 may include a substantially horizontal opening or recess, which can enable head portion 11, which is coupled to unitary pivoting mechanism 13 via coupling mechanism 50, to pivot relative to unitary pivoting mechanism 13 horizontally. Similarly, coupling mechanism 51 may include a substantially vertical opening or recess, which can enable handle portion 14, which is coupled to unitary pivoting mechanism 13 via coupling mechanism 51, to pivot relative to unitary pivoting mechanism 13 vertically. Accordingly, the size, shape, and orientation of coupling mechanisms 50 and 51 may dictate the type, size, and range of motion between unitary pivoting mechanism 13 and head portion 11 and handle portion 14. As shown in FIG. 6, coupling mechanisms 50 and 51 can be substantially orthogonal to one another. Alternatively, coupling mechanisms 50 and 51 can be oriented in various angles depending on the pivoting motion that is desired. Accordingly, coupling mechanisms 50 and 51 can include any shape, size, orientation, or mechanism that enables the desired relative motion between unitary pivoting mechanism 13 and head portion 11 and handle portion 14.

The embodiments and examples shown above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of the disclosure. For a better understanding of the disclosure, reference should be had to the accompanying drawings and descriptive matter in which there is illustrated exemplary embodiments of the present invention.

What is claimed:

1. An abrasive skin treatment device comprising:
   a unitary pivoting mechanism having a first end with first pivoting joint and a second end with a second pivoting joint;
   a handle portion coupled to the first end of the unitary pivoting mechanism such that the first pivoting joint enables the handle portion to pivot relative to the unitary pivoting mechanism along a first plane while substantially preventing the handle portion from pivoting relative to the unitary pivoting mechanism along a second plane; and
   a head portion including an exfoliating element, the head portion coupled to the second end of the unitary pivoting mechanism such that the second pivoting joint enables the head portion to pivot relative to the unitary pivoting mechanism along the second plane, the first plane and the second plane being different.

2. The device of claim 1, wherein the unitary pivoting mechanism is substantially spherical.

3. The device of claim 1, wherein the head portion includes a light.

4. The device of claim 3, wherein the light includes a light emitting diode.

5. The device of claim 1, wherein the exfoliating element is removably coupled to the head portion.

6. The device of claim 1, wherein the exfoliating element is rotatably coupled to the head portion.

7. The device of claim 1, further comprising a motor and power supply.

8. The device of claim 1, wherein the head portion pivots about the unitary pivoting mechanism relative to the handle portion upon application of a force to at least one of the head portion and the handle portion.

9. The device of claim 1, wherein the exfoliating element is substantially cylindrical.

10. The device of claim 1, wherein the unitary pivoting mechanism substantially prevents the head portion from pivoting relative to the unitary pivoting mechanism along the first plane.

\* \* \* \* \*